US00PP12836P2

(12) United States Plant Patent
Hlubik

(10) Patent No.: US PP12,836 P2
(45) Date of Patent: Aug. 6, 2002

(54) **PLANT VARIETY OF *LONICERA×BROWNII* NAMED 'KRISTIN'S GOLD'**

(75) Inventor: Stephen Hlubik, Davis, CA (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/516,305

(22) Filed: Feb. 29, 2000

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Anne Marie Grünberg
(74) *Attorney, Agent, or Firm*—Christie, Parker & Hale, LLP

(57) ABSTRACT

A new plant variety of *Lonicera×brownii* characterized by its bright yellow flowers.

2 Drawing Sheets

BACKGROUND OF THE INVENTION

The present invention relates to a new and distinct variety of *Lonicera×brownii* (Regel) Carriere which was discovered as a branch sport in a controlled planting of *Lonicera×brownii* 'Dropmore Scarlet' by Mr. Stephen Hlubik, in Vacaville, Calif. The varietal denomination of the new variety is 'KRISTIN'S GOLD'.

The genus Lonicera is included in the family Caprifoliaceae which comprises about 15 genera of shrubs growing in the northern and southern hemispheres. Lonicera comprises over 200 species of deciduous or evergreen shrubs, many of which possess desirable ornamental characteristics. *Lonicera×brownii* is a hybrid of *Lonicera sempervirens* and *Lonicera hirsuta* (Eaton). The typical form of the cross took place in 1853. It generally is a deciduous shrub or vine growing to 3 meters tall. Leaves are elliptic, blue green and pubescent on the underside, and opposite on the stems. Flowers typically bloom in the spring and summer.

Flowers of *Lonicera×brownii* are somewhat "2 lipped", in auxiliary pairs subtended by 2 bracts and 4 bractlets in sessile whorls at the ends of the branches. Known cultivars include 'Fuchsioides' with flowers that are scarlet on the outside; 'Plantierensis' with coral red flowers with scarlet lobes; 'Punicea' with orange-red flowers; 'Dropmore Scarlet' with bright scarlet flowers; and 'Youngii' with deep crimson red flowers.

SUMMARY OF THE INVENTION

The new variety was discovered as a branch sport in a controlled planting of *Lonicera×brownii* 'Dropmore Scarlet' and differs from its parent in having bright yellow flowers. Asexual reproduction of the new variety by stem cuttings, performed in Vacaville, Calif. have confirmed that the distinctive characteristics of the new variety are stable and transmitted to succeeding generations, and the new variety reproduces true to type.

COMPARISON WITH PARENTS

'KRISTIN'S GOLD' is distinguished from its parent and all other varieties of *Lonicera×brownii* of which I am aware in having bright yellow flowers, in contrast to the crimson to orange-red flowers of its parent.

BRIEF DESCRIPTION OF ILLUSTRATIONS

The accompanying photographic illustrations show a specimen of the new cultivar as true to color as is reasonably possible to make in an illustration of this character.

First sheet illustrates interior parts of the flower of 'KRISTIN'S GOLD'.

Second sheet illustrates exterior parts of the flower of 'KRISTIN'S GOLD'.

DETAILED DESCRIPTION OF THE NEW VARIETY

'KRISTIN'S GOLD' has not been observed under all possible environmental, cultural, and light conditions. The following observations and descriptions are of plants grown in containers at Vacaville, Calif. In this description, color references are to *The Royal Horticultural Society Colour Chart*(1995) and terminology used in the color descriptions herein refers to plate numbers in this color chart. Phenotypic expression may vary with light intensity, cultural, and environmental conditions.

CLASSIFICATION

Botanical: *Lonicera×brownii* (Regel) Carriere 'KRISTIN'S GOLD'.

Parentage: Branch sport of *Lonicera×brownii* 'Dropmore Scarlet'.

Propagation: By vegetative cuttings.

PLANT

Size: Mature plant can climb and spread to about 10 meters at maturity.

Habit: A scrambling, twining vine that can be grown on the ground, or allowed to climb screens or trellises.

Branching

Leaf description:

*Arrangement.*—Simple, opposite on stems.

*Leaf shape.*—Ovate to nearly elliptic. Apex: Obtuse to nearly rounded, occasionally acute.

*Base leaf size.*—Approximately 1.5 to 3 cm wide and 3 to 5 cm long.

*Leaf margin.*—Entire.

*Leaf texture and substance.*—Adaxial: Smooth, often slightly undulate. Abaxial: Somewhat pubescent.

*Immature leaf color.*—Adaxial: Near Green Group 138B. Abaxial: Near Greyed-Green Group 189C. Midrib: Greyed-Green Group 189D.

*Mature leaf color.*—Adaxial: Near Green Group 137A. Abaxial: Near Greyed-Green Group 189B.

*Stem color.*—Near Greyed-Purple Group 187C.

Petioles:

*Size.*—Approximately 0.5 mm long.

*Color.*—Near Red Group 45C.

Hardiness: USDA Zone 5 (−20° F. to −10° F.).

Vigor: 4 to 6 feet per year.

Pests/diseases: No pest or disease problems noted.

INFLORESENCE

Bloom period: Early summer to fall.

Lastingness of individual bloom: 2 to 3 weeks.

Flower form: Capitulum.

Shape of inflorescence: Tubular, flared and divided at end of the lobes.

Flower arrangement: Paired in leaf axils, sometimes crowed at tips of branches.

Flower size: Approximately 3.5 to 4 cm long.

Color: Inside of tube near Yellow-Orange Group 21A to 21B; unopened bud and outer base of tube near Yellow Group 12B.

Buds:

*Shape.*—Club shaped.

*Size.*—Approximately 2 cm long and 2 mm in diameter.

Peduncles: Very short (flower almost sessile).

Fragrance: None noted.

REPRODUCTIVE ORGANS

Stamens: 5; near Yellow-Orange Group 19C.

Pistils: 1; near Yellow-Orange Group 19C.

Stigma: Near Yellow-Orange Group 19C.

Fruit: Blue-black berry produced from November to December, near Red Group 42A to 42B; 6 to 7 mm wide.

I claim:

1. A new variety of *Lonicera×brownii* plant substantially as shown and described.

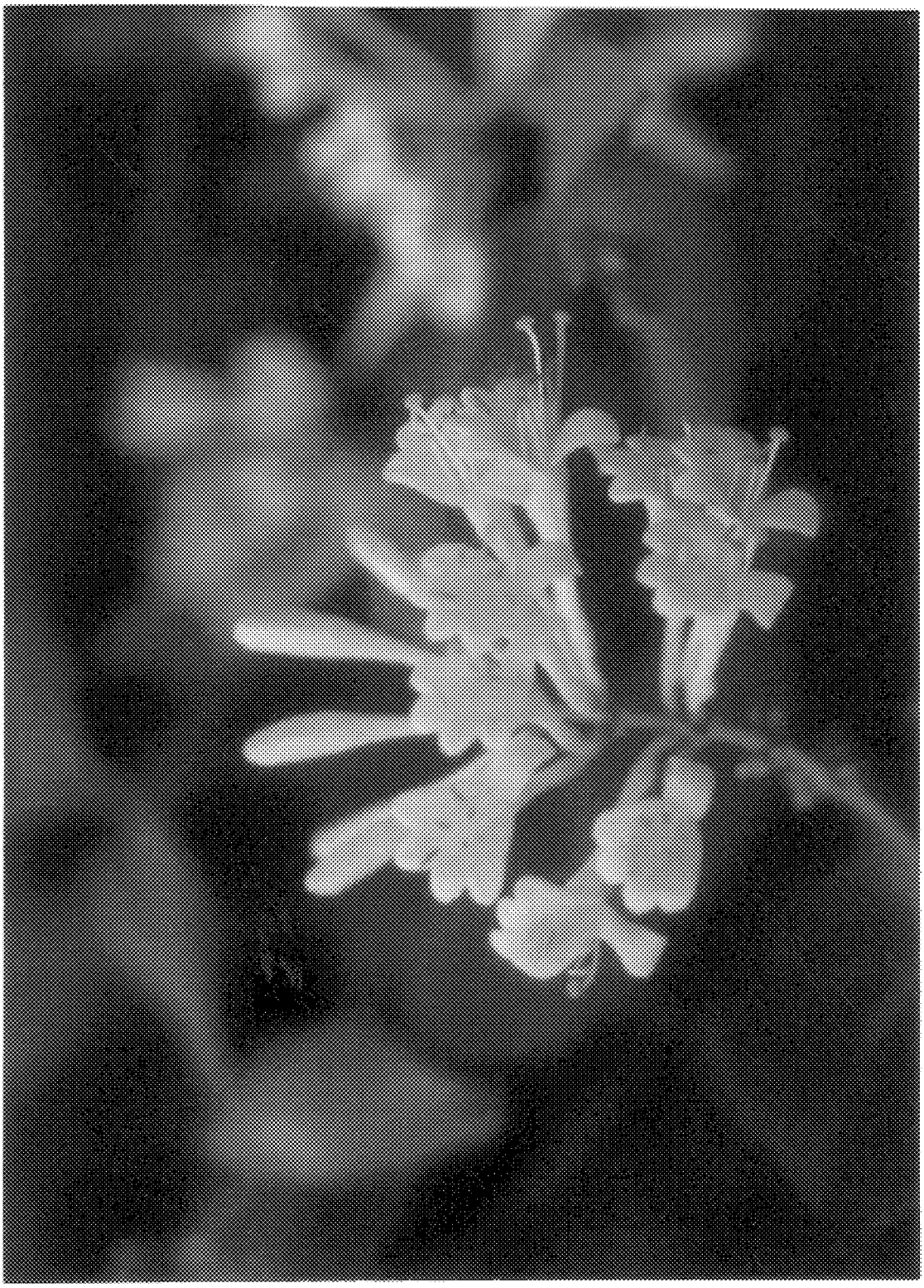

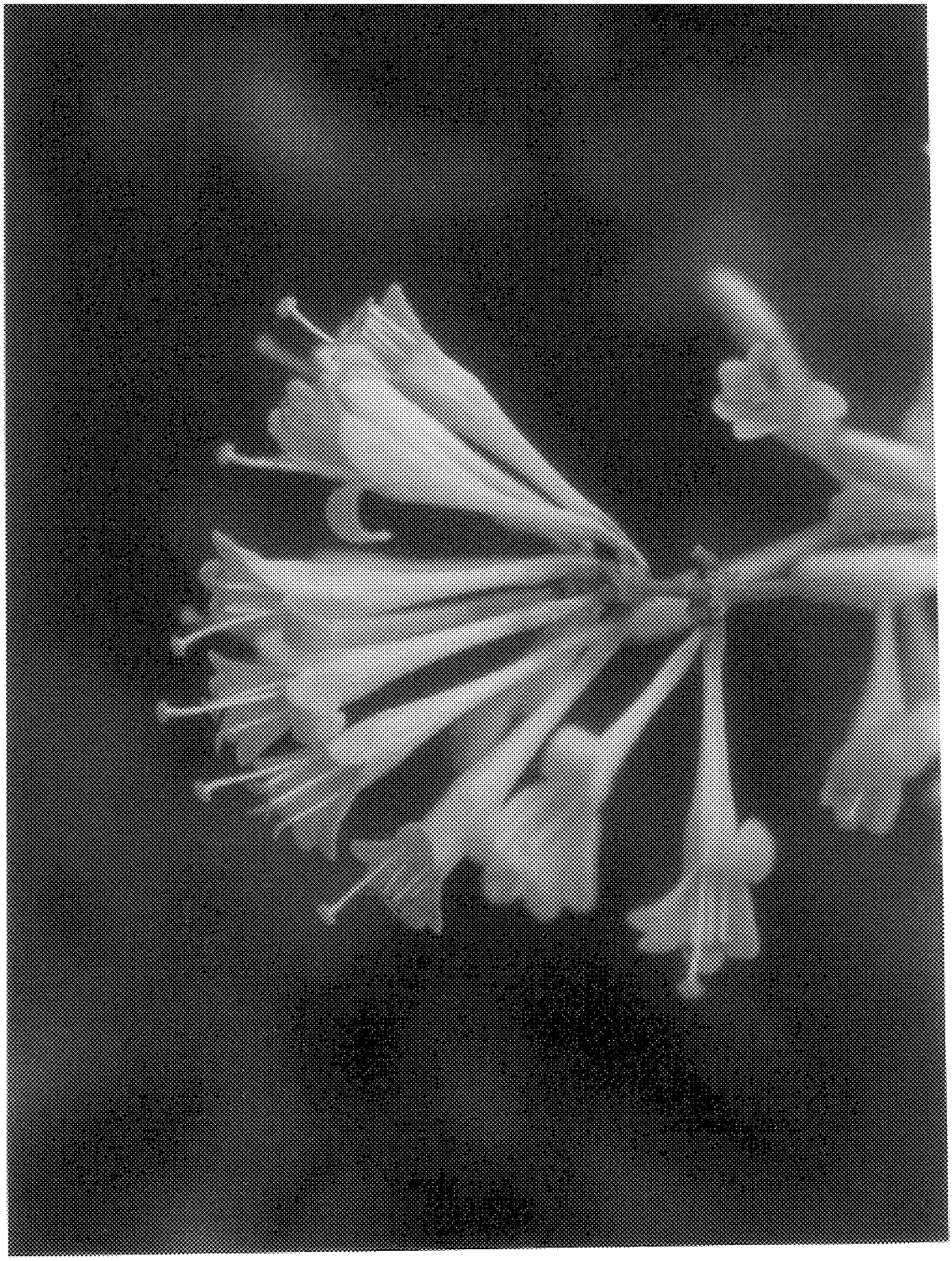

* * * * *